United States Patent [19]
Lathrop, Jr. et al.

[11] Patent Number: 5,555,897
[45] Date of Patent: Sep. 17, 1996

[54] PERITONEAL DISTENSION ROBOTIC ARM

[75] Inventors: Robert L. Lathrop, Jr.; Rick E. Emerson, both of San Jose; James E. Wiley, Los Gatos; James M. Sklenar, Santa Cruz; Albert K. Chin, Palo Alto; Frederick H. Moll, San Francisco; David Forster, Woodside, all of Calif.

[73] Assignee: Origin Medsystems, Inc., Menlo Park, Calif.

[21] Appl. No.: 308,030

[22] Filed: Sep. 16, 1994

Related U.S. Application Data

[62] Division of Ser. No. 899,556, Jun. 16, 1992, Pat. No. 5,372,147.
[51] Int. Cl.$^6$ ........................................ A61G 15/00
[52] U.S. Cl. ............................ 128/845; 600/201
[58] Field of Search ........................... 128/845, 897; 600/201, 215, 216, 219, 235, 231, 238; 5/630, 648, 658, 661, 662

[56] References Cited

U.S. PATENT DOCUMENTS

| | | | |
|---|---|---|---|
| 3,810,462 | 5/1974 | Szpur | 600/201 |
| 4,971,037 | 11/1990 | Pelta | 600/201 |

OTHER PUBLICATIONS

Marshall et al., "New, table–supported, self–retaining retractor" Surgery, Sep. 1963.

*Primary Examiner*—Angela D. Sykes
*Assistant Examiner*—John P. Lacyk
*Attorney, Agent, or Firm*—Townsend and Townsend and Crew LLP

[57] ABSTRACT

The invention provides an apparatus and method for manipulating parts of the body in surgical procedures, particularly useful for peritoneal distension in laparoscopic surgery. The apparatus comprises a positionable support structure having an extendible horizontal arm rotatably mounted to an extendible vertical post, the post having a clamp at its lower end for mounting to a surgical table. An end segment at the distal end of the horizontal arm has a mount for mounting end-of-arm tooling, for example, peritoneal distension instruments. Locking mechanisms are disposed in the horizontal arm, vertical post and end segment to lock the support structure in a desired position. A motor is disposed within the vertical post for power-assisted extension and retraction of the vertical post. Preferably, the locking mechanisms and motor are controllable using switches mounted on the end segment. The method comprises providing a support structure as described mounted to a surgical table, positioning the distal end of the horizontal arm over a patient on the table, activating locking mechanisms in the horizontal arm and vertical post to lock the support structure in position, attaching peritoneal distension instruments to the distal end of the horizontal arm, and vertically extending the vertical post while the horizontal arm remains locked relative to the post, thereby distending the peritoneum of the patient.

32 Claims, 13 Drawing Sheets

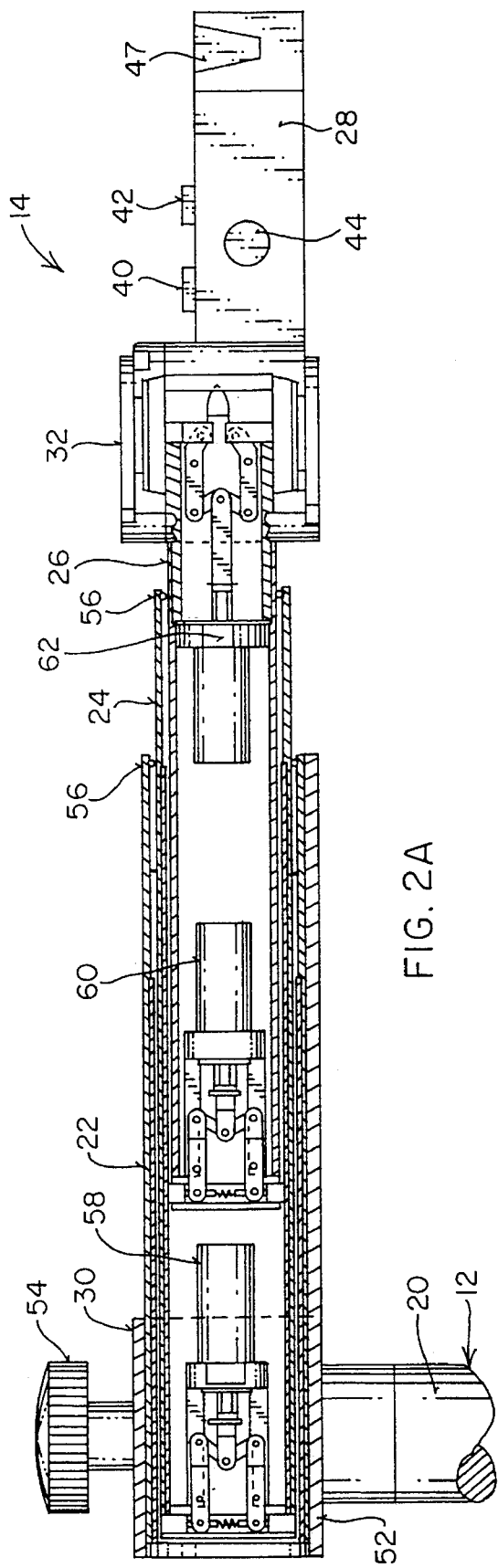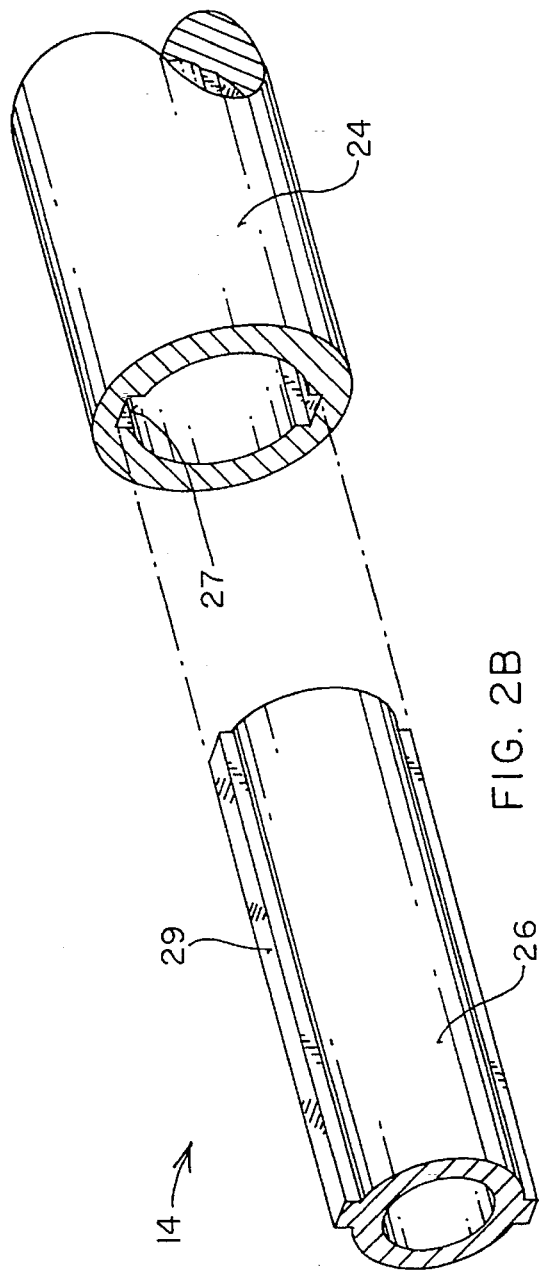
FIG. 2A
FIG. 2B

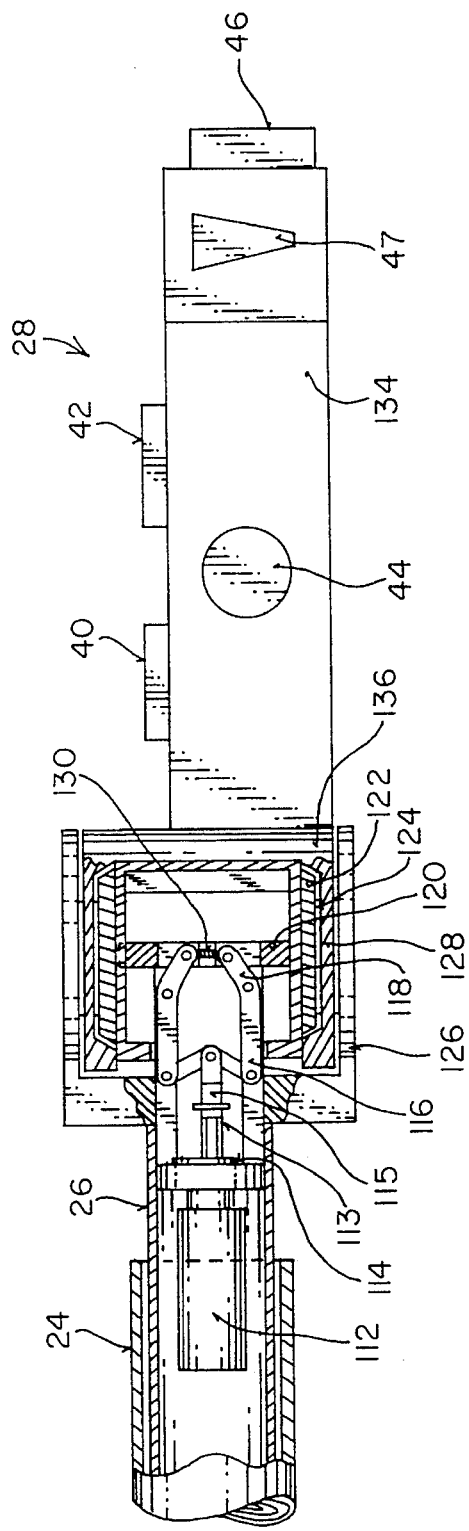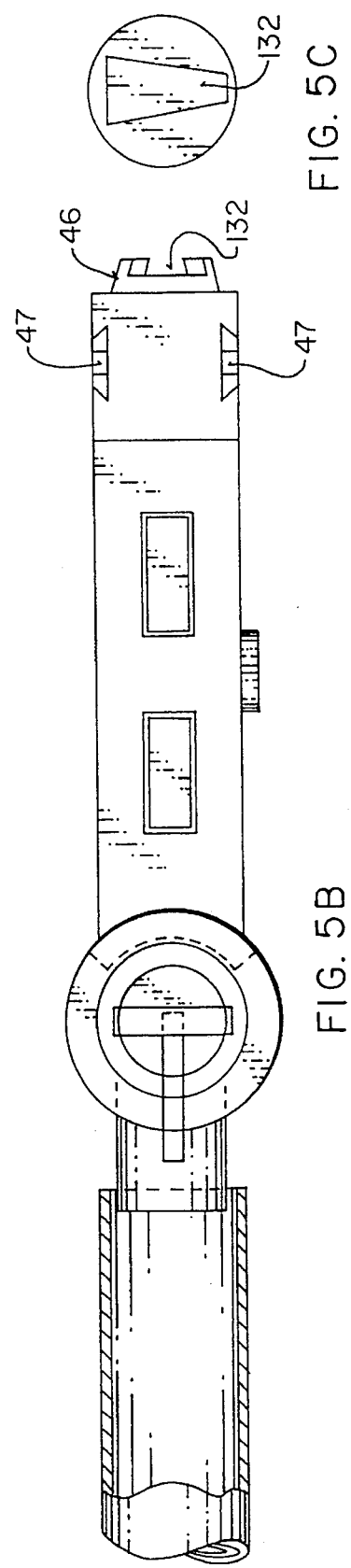
FIG. 5A
FIG. 5B
FIG. 5C

PERITONEAL DISTENSION ROBOTIC ARM

This is a Division of application Ser. No. 07/899,556 filed Jun. 16, 1992 now U.S. Pat. No. 5,372,147.

BACKGROUND OF THE INVENTION

The present invention relates generally to the structure and use of surgical instruments and, more particularly, to positionable support structures for manipulating parts of the body in surgical procedures.

Laparoscopic surgery is generally performed through small incisions in the abdomen using specialized instruments to accomplish the desired surgical procedure. Usually, the instruments are introduced through a narrow diameter tube, such as a trocar sleeve, while the physician observes manipulation of the instruments through specialized imaging equipment, such as a laparoscope. Laparoscopic surgical techniques offer significant advantages over conventional "open" surgical procedures. In particular, the laparoscopic techniques are usually less traumatic, require a shorter recovery time, and are less costly than corresponding conventional surgical procedures.

In laparoscopic surgical procedures, it is generally necessary to lift the abdominal wall away from the underlying abdominal organs to improve the visibility and accessibility of such organs. Such distension of the abdominal cavity, or peritoneum, has been heretofore accomplished by injecting a gas such as $CO_2$ into the peritoneal cavity to tent-up the interior of the abdominal wall. Such "insufflation" requires gas seals to be present at all entry ports through the abdominal wall; and, because of the doming effect on the abdomen, the laparoscopic instruments (graspers, scissors, electrocautery instruments, etc.) need long shafts (on the order of 12"–13") to reach the treatment site. Such instruments are difficult to control and result in exaggerated movements during instrument application. Further, using the insufflation technique, maintenance of the required distension is complicated by the loss of gas through the entry ports through the abdominal wall.

It has been proposed to use a mechanical system for peritoneal distension to overcome the problems associated with the insufflation technique. For example, co-pending U.S. application Ser. No. 07/706,781, filed May 29, 1991, entitled "Apparatus and Method for Peritoneal Retraction," the full disclosure of which is incorporated herein by reference, describes a technique for lifting the abdominal wall by means of angle-shaped rods having elongated arms at their distal ends which are inserted through an incision and fanned out within the abdomen. A mechanical lifting arm mounted to the surgical table is positioned over the patient and coupled to the rods, and lifting is accomplished by activating a motor in the arm. Such mechanical systems must be readily manipulable by the treating physician. In particular, such a mechanical lifting arm must be (1) horizontally positionable over the desired site, and (2) vertically adjustable to raise the abdominal wall in a controlled manner.

For these reasons, it would be desirable to provide improved methods and apparatus for mechanical manipulation of body structures, particularly for distending the peritoneal cavity during laparoscopic surgical procedures. In particular, the methods and apparatus should provide for controlled lifting of the abdominal wall or other body structure, preferably using power-assisted lifting and lowering. The methods and apparatus should allow manipulation of body structures by a single person, and should be simple to operate. The apparatus should have convenient controls, preferably located in the immediate vicinity of the surgical working area, most desirably immediately above the working area. The methods and apparatus should further have application in surgical facilities not equipped with pneumatic or hydraulic supply lines, and should provide for patient and operator safety in the event of a power failure. It would also be particularly desirable if the methods and apparatus were suitable for performing manipulation of body structures other than the peritoneum in other types of surgical procedures.

DESCRIPTION OF THE BACKGROUND ART

U.S. Pat. No. 4,807,618 describes a device for holding part of a patient's body, such as a limb or organ, in various positions required by a surgeon for the performance of a surgical procedure. The device is a segmented arm, clamped to a surgical table, with a grasping device affixed to its end for attaching to a patient's body part. Each segment of the arm is connected by ball and socket joints with pneumatic braking mechanisms to lock the arm in position.

U.S. Pat. No. 4,791,934 describes a system for performing surgery using diagnostic mapping data generated by a CT scanner. The system utilizes a surgical instrument mounted to a guide which clamps to the rail of a surgical table, allowing the instrument to be positioned at a selected point on the patient's body.

U.S. Pat. No. 4,787,813 describes an industrial robot for use in clean room environments, the robot including a rotatable arm which may be raised and lowered with respect to a base.

U.S. Pat. No. 4,979,949 describes a robotic system for aiding in the performance of surgical bone alterations. The system includes a robot mounted to or near a surgical table used for precisely locating a surgical tool over a selected part of a patient's body.

U.S. Pat. No. 4,989,253 describes a voice-activated control system for positioning a microscope over locations on the patient's body. The system includes a motorized structural support member to which a microscope is mounted and which can be controlled through the voice commands of the user.

U.S. Pat. No. 4,904,514 describes a system for draping a mechanical linkage, such as a robot, so as to protect the linkage from contaminating material in the surrounding environment.

U.S. Pat. No. 4,604,016 describes a hand controller for the actuation of a remote apparatus, wherein the hand controller translates forces encountered by the apparatus to a hand held cursor thereby providing interactive cursor force feedback.

U.S. Pat. No. 4,445,184 describes an articulated robot which includes a number of articulated joints with motors and braking mechanisms.

SUMMARY OF THE INVENTION

According to the present invention, improved apparatus and methods are provided for manipulating body structures during surgical procedures, especially for distending the abdominal cavity during laparoscopic surgical procedures. The apparatus comprise a support structure including an extendible vertical post, an extendible horizontal arm, and means at the lower end of the post for mounting the structure to a surgical table. A mechanism is provided for releasably locking the position of the horizontal arm relative to the vertical post (i.e., radial distance and angle of rotation relative to the vertical axis defined by the post) preferably including an actuator switch at the distal end of the horizontal arm. Thus, the treating physician can vertically align the distal end of the horizontal arm over a desired location using a single hand which both actuates the switch and manipulates the end of the arm. A mechanism is further provided for power-assisted raising and lowering of the vertical post. In this way, after the horizontal arm has been properly aligned (and external instrument connections are made as described below), the arm can be raised to perform a desired physical distension or other manipulation. Preferably, an actuation switch for the raising and lowering mechanism is disposed or the distal end of the horizontal arm to further facilitate control by the physician.

In the exemplary method of the present invention, the horizontal arm is positioned over a patient on the table, and the locking mechanisms on the horizontal arm and vertical post are activated to lock the arm in position. Surgical instruments adapted for coupling to the abdominal cavity or other body structures are then attached to the distal end of the horizontal arm and the arm is raised vertically, usually by pressing a switch on the end segment to activate the motor, lifting the abdominal wall or other body structures of the patient. The positionable support structure is easily manipulated by the user simply by grasping the arm and moving it to the desired location. Power assisted raising of the arm provides quick and controlled lifting of the body structure. Moreover, in laparoscopic surgery, the use of such a positionable support structure eliminates the need for gas insufflation, and the associated problems of gas loss through entry ports to the abdominal cavity and doming of the abdomen. Further, the degree of distension can be carefully controlled to minimize traumatic impact on the patient.

In a first preferred aspect of the present invention, the positionable support structure includes a number of telescoping segments in both the horizontal arm and vertical post. Electric solenoid-activated locking mechanisms are mounted within each segment of the arm to lock it in a radial position. Another solenoid-activated rotational locking mechanism is located in the uppermost segment of the vertical post. Preferably, the locking mechanisms are biased in a locked position when no power is applied, and are deactivated by switches located at the distal end of the horizontal arm, at a point where the arm would typically be grasped by the user for positioning. This allows the arm to be quickly positioned and locked using one hand.

The positionable support structure further includes an electric motor situated within the vertical post which drives a linear drive mechanism for extending the vertical post. The electric motor is actuated, like the locking mechanisms, using a switch located at the distal end of the horizontal arm for accessibility and safety. The support structure further includes a clamping mechanism configured to mount on the mounting rail of a surgical table. Preferably, the clamping mechanism has a universal design so as to fit a variety of surgical tables.

In a preferred embodiment, the motor and solenoid locking mechanisms are electric, allowing the support structure to be used in a surgical facility not having pneumatic or hydraulic supplies, or where the use of such supplies would be undesirable.

In another embodiment, rather than having the electric locking mechanisms mounted in the horizontal arm, the arm is locked in radial position by loading the distal end of the arm, i.e. by lifting the body structure. This creates bending and friction forces in each joint of the telescoping segments which prevent the segments from moving relative to each other.

The support structure, in a preferred embodiment, further includes means for draping the structure so as to provide sterility.

The support structure usually will have an end segment, which is pivotally attached to the distal end of the horizontal arm. In a preferred embodiment, the switches for the locking mechanisms and the motor are located on the end segment. The end segment further includes means for mounting surgical instruments to the end segment. In a preferred embodiment, such means will comprise a tapering dovetail aperture into which a surgical tool with a corresponding configuration can be mounted. Tapering the aperture from wide at the top to narrow at the bottom of the aperture provides a self-relieving feature for improved safety. Such a configuration allows a tool mounted to the end segment to be pushed vertically upward if any upward force is encountered by the tool, such as when the support structure is lowered toward a patient's body.

Preferably, the support structure includes a load sensor providing feedback of the loading borne by the end segment. In a further preferred embodiment, the support structure includes means for stopping upward vertical motion of the arm when a given load limit is exceeded.

BRIEF DESCRIPTION OF THE DRAWINGS

FIG. 2A is a side cross-sectional view of the horizontal arm of the positionable support structure of FIG. 1.

FIG. 2B is a perspective assembly view of two segments of the horizontal arm of FIG. 2A.

FIGS. 5A–5C are top, side elevational, and end views of an end segment of the horizontal arm of the positional support structure of FIG. 1.

DETAILED DESCRIPTION OF THE ILLUSTRATIVE EMBODIMENTS

Figure 1A:
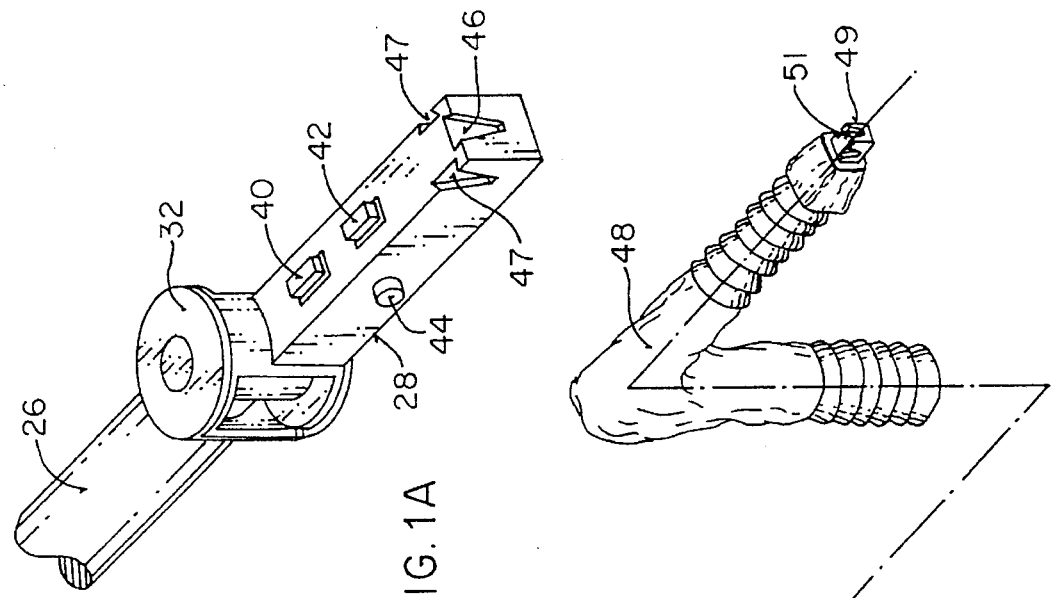
FIG. 1A is a detailed view of the distal end of a horizontal arm of the structure of FIG. 1.

The apparatus and method of the present invention are useful for manipulating a variety of body structures in surgical procedures. In particular, the apparatus and method of the present invention are useful for lifting the abdominal cavity, or peritoneum, off of the underlying abdominal organs for improved visibility and accessibility in laparoscopic surgery when used in combination with the apparatus and method described in co-pending application Ser. No. 07/706,781, the disclosure of which has previously been incorporated herein by reference. However, the method and apparatus of the present invention are by no means limited to providing peritoneal distension in laparoscopic surgery, and are useful in a variety of procedures where a positionable support structure providing controlled upward lifting would have application. For example, the positionable support structure could be used for holding a limb or organ in position during a surgical procedure, such as shoulder or knee surgery. Further, the positionable support structure could be used for holding a limb or organ in a desired position for taking x-rays or conducting an examination.

The method of the present invention utilizes a positionable support structure including an extendible vertical post and an extendible horizontal arm. The distal end of the horizontal arm is first horizontally aligned at a desired location over a patient's body typically by rotating radially extending the arm relative to the axis of the vertical post. Locking mechanisms in the arm and post are then actuated to hold the arm in position relative to the post. Specialized instruments adapted to the particular surgical procedure being performed are then attached to the distal end of the horizontal arm. Such instruments could comprise, for example, peritoneal distension instruments coupled to the peritoneal cavity of the patient. The vertical post is then raised using a powered vertical extension and retraction mechanism to provide a controlled lifting of the body structure, usually the peritoneum. When the horizontal arm and the attached instrument in the body structure have been lifted to the desired location and shape, the surgical procedure may be performed while the support structure remains locked in position to maintain the body structure in the desired position.

Preferably, a switch or equivalent actuator is disposed at the distal end of the horizontal arm so that the support structure can be positioned easily by grasping the horizontal arm and moving its distal end over the desired point on the patient's body. In a preferred embodiment, the vertical extension means and locking means can be activated using switches at the distal end of the horizontal arm. This permits the user to position, lock and lift the support structure using one hand without having to change positions or move his or her hand.

The positional locking of the horizontal arm of the support structure is preferably accomplished using electric solenoid-activated locking mechanisms disposed within the horizontal arm and vertical post, the locking mechanisms in the arm resisting extension or retraction of the arm and the locking mechanism in the vertical post resisting rotation of the arm relative to the post. Usually, the locking mechanisms will be configured to be in a "locked" position when no power is applied to the solenoid, so as to maintain the position of the support structure in the event of a power failure.

Preferably, the vertical post and horizontal arm include a plurality of telescoping segments, the locking mechanisms of the arm being mounted within each segment and fictionally engaging the interior wall surface of the adjacent segment. Each segment will usually include means for preventing rotational movement relative to the adjacent segment, which preferably comprise a longitudinal channel in the interior of each segment which engages with a radially-extending tongue on the exterior of the adjacent segment.

In a preferred embodiment, the support structure includes an end segment pivotally attached to the distal end of the horizontal arm, including a locking mechanism for locking the end segment into position relative to the horizontal arm. The end segment will usually have means for mounting surgical instruments to its distal end. Preferably, this means for mounting will be configured so as to permit a surgical instrument mounted on the end segment to move vertically upward in the event the instrument encounters and upward vertical force. This provides a safety feature preventing the application of excessive downward force on the patient. In the preferred embodiment, the end segment also includes actuator switches for actuating the locking means and lifting means of the support structure.

The support structure will usually be mountable to a surgical table, preferably to the mounting rail which is of a standard size and shape for a variety of surgical tables. The means for mounting includes a clamp which allows the support structure to be rigidly clamped in position at a desired point along the rail. Preferably the clamp can be quickly applied and released to allow the support structure to be moved along the rail or removed altogether with little time or effort required.

The support structure preferably includes means for draping the structure so as to maintain sterility in the surgical environment. The draping means usually will cover substantially all of the support structure, and be capable of quick and convenient installation and removal.

Figure 1:
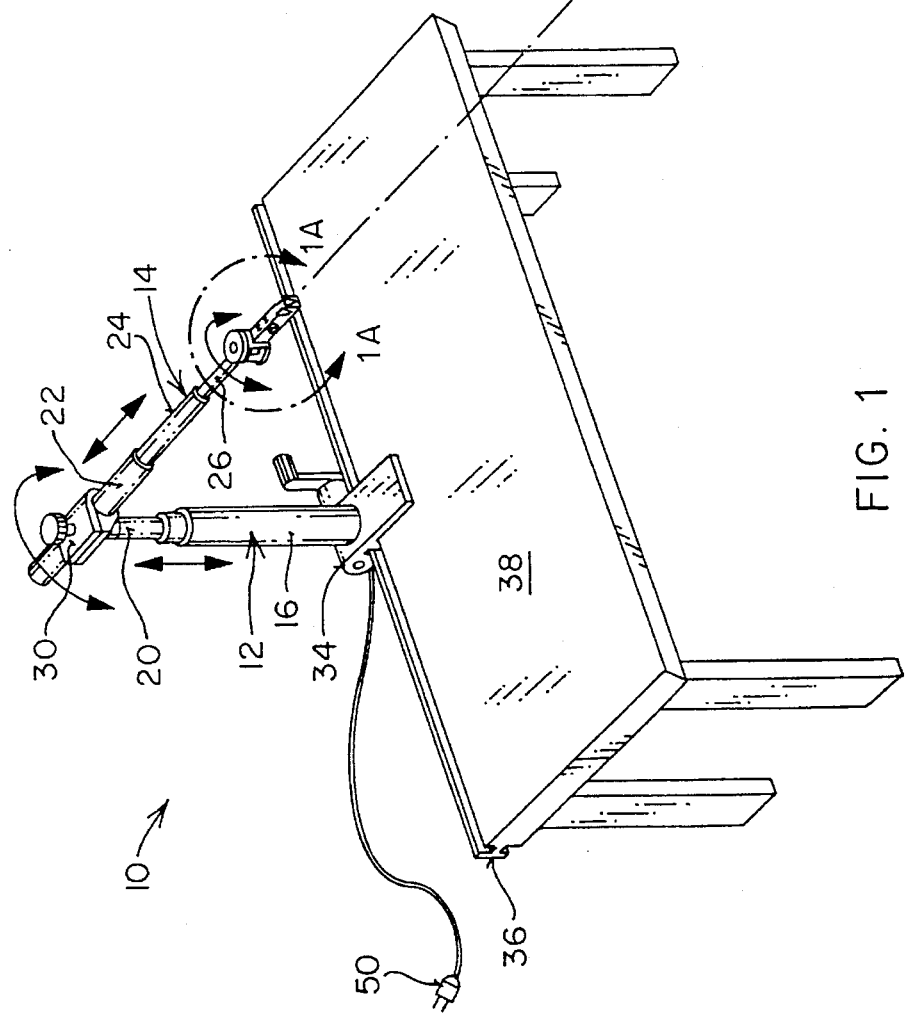
FIG. 1 is a perspective view of a positionable support structure constructed according to the principles of the present invention, mounted to a table.

Referring now to FIG. 1, a first embodiment of a positionable support structure constructed in accordance with the principles of the present invention will be described. The support structure 10 includes a vertical post 12 and horizontal arm 14, each having a plurality of telescoping segments 16, 18, 20, 22, 24, 26. Mounted at the distal end of horizontal arm 14 is end segment 28. Horizontal arm 14 is pivotally attached to vertical post 12 by frame 30 affixed to the top end of upper segment 20 of vertical post 12. The support structure 10 is mounted to a surgical table 38 by clamping means 34. The clamping means 34 is configured to engage a conventional mounting rail 36 of surgical table 38. The end segment is attached to horizontal arm 14 by a rotatable joint 32. The end segment includes mounting aperture 46, in a tapered dovetail configuration. Side mounts 47 are provided for mounting additional tooling. End segment 28 further includes switching means 40, 42 for raising and lowering the horizontal arm. Also disposed on end segment 28 is switch 44 for selectively releasing the horizontal arm locking means as described below. During surgical procedures, the support structure will be covered by draping means 48. Power for driving the lifting means and the locking means of the support structure is provided through a power cord 50.

In a preferred embodiment, draping means 48 comprises a flexible, contaminant resistant impervious material, such as flexible thermoplastic, having resilient gathered portions around the horizontal arm and vertical post to allow extension and retraction. Preferably, draping means 48 has an attachment 49 at its horizontal distal end which allows user accessibility to switching means 40, 42, 44, while sealing off arm 14 and end segment 28. In an exemplary embodiment, proximal portion of attachment 49 engages with dovetail mount 46, while allowing surgical instruments to be mounted in apertures 51 at the distal end and on the lateral sides of attachment 49. Draping means 48 along with attachment 49 will usually be disposable or sterilizable, to permit use in a sterilized surgical environment.

Referring now to FIG. 2, the horizontal arm 14 of the support structure will be described. Segment 22 of horizontal arm 14 is mounted at the top of segment 20 of vertical post 12 through collar 52 in frame 30, preferably providing radial adjustability of horizontal arm 14. Usually the segment 22 is fixed in a desired position by tightening knob 54 which clamps collar 52 around the perimeter of segment 22. Alternatively, arm 14 may be non-adjustably fixed to post 12 by a fixed mount in place of collar 52. Or, other means of adjustment may be used in place of knob 54, such as a button or ball-type detent in arm 14 which nests in a hole or notch in collar 52, wherein multiple holes or notches spaced radially along the collar allow radial adjustment of the arm.

Segment 24 is slidably disposed within segment 22, the segment 24 having an exterior diameter just smaller than the interior diameter of segment 22. Similarly, segment 26 is slidably disposed within segment 24, the exterior diameter of segment 26 being slightly smaller than the interior diameter of segment 24. At the distal ends of both segments 22 and 24 are bearings 56 which reduce friction between segments 26 and 24 and segments 24 and 22.

In an exemplary embodiment, bearings 56 and the surface finish of segments 22, 24, 26 are selected such that the frictional resistance against distal-most segment 26 is less than that against segment 24. In this way, when the horizontal arm is extended distally, distal-most segment 26 is extended fully before segment 24 is extended. Thus, the segment having the smallest diameter and lowest profile is used first, with the larger segments being extended into the work area only if needed. Locking mechanisms 58 and 60 are mounted at the proximal ends of segments 26 and 24 to provide frictional engagement with the interior walls of segments 22 and 24, respectively. End segment locking mechanism 62 is disposed at the distal end of segment 26 and fictionally engages end segment 28 so as to lock it in position. The structure and operation of the locking mechanisms will be described more fully below.

Figure 3:
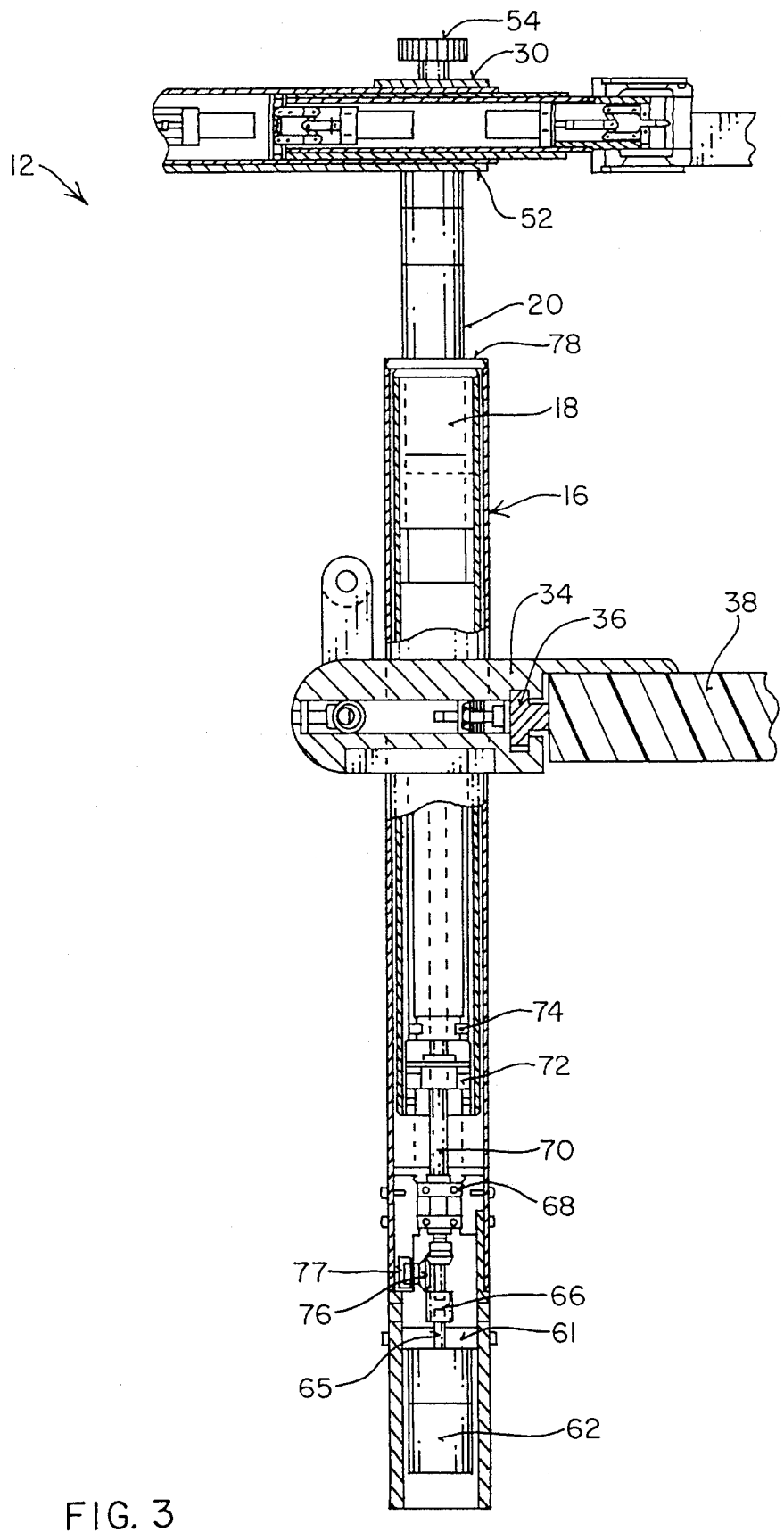
FIG. 3 is a side cross-sectional view of the vertical post of the positional support structure of FIG. 1.

Referring now to FIG. 3, the structure of vertical post 12 will be more fully described. Like horizontal arm 14, vertical post 12 includes three telescoping segments 16, 18, 20, with bearings 78 disposed at the upper end of segments 16 and 18. Frame 30, to which horizontal arm 30 is mounted, is rigidly affixed to the upper end of segment 20. Electric motor 62 is fixed to mount 64 disposed in the lower end of segment 16. Motor shaft 65 is coupled to lead screw 70 through coupler 66. Gears 76 geared to lead screw 70 permit the lead screw to be turned manually by attaching a handle through aperture 77 to gears 76. Lead screw 70 is supported through bearings 68. Nuts 72, 74 fixed to the interior walls of segments 18, 20 translate segments 18 and 20 vertically upward or downward when shaft 65 of motor 62 is rotated. Vertical post 16 is mountable to a surgical table 38 by clamp mechanism 34 rigidly fixed to segment 16. In a preferred embodiment, clamp mechanism 34 is configured to clamp to a standard rail 36, common on a variety of surgical tables. The structure and use of the clamping mechanism 34 will be described more fully below.

Each of segments 16–26 usually includes means for preventing the rotation of the telescoping segments relative to each other. As illustrated in FIG. 2B, the means for preventing rotation may comprise a longitudinal keyway 27 extending the length of each segment along its interior wall with a corresponding tongue 29 extending laterally from the proximal end of the adjacent segment, tongue 29 slidably engaging in keyway 27.

Figure 4:
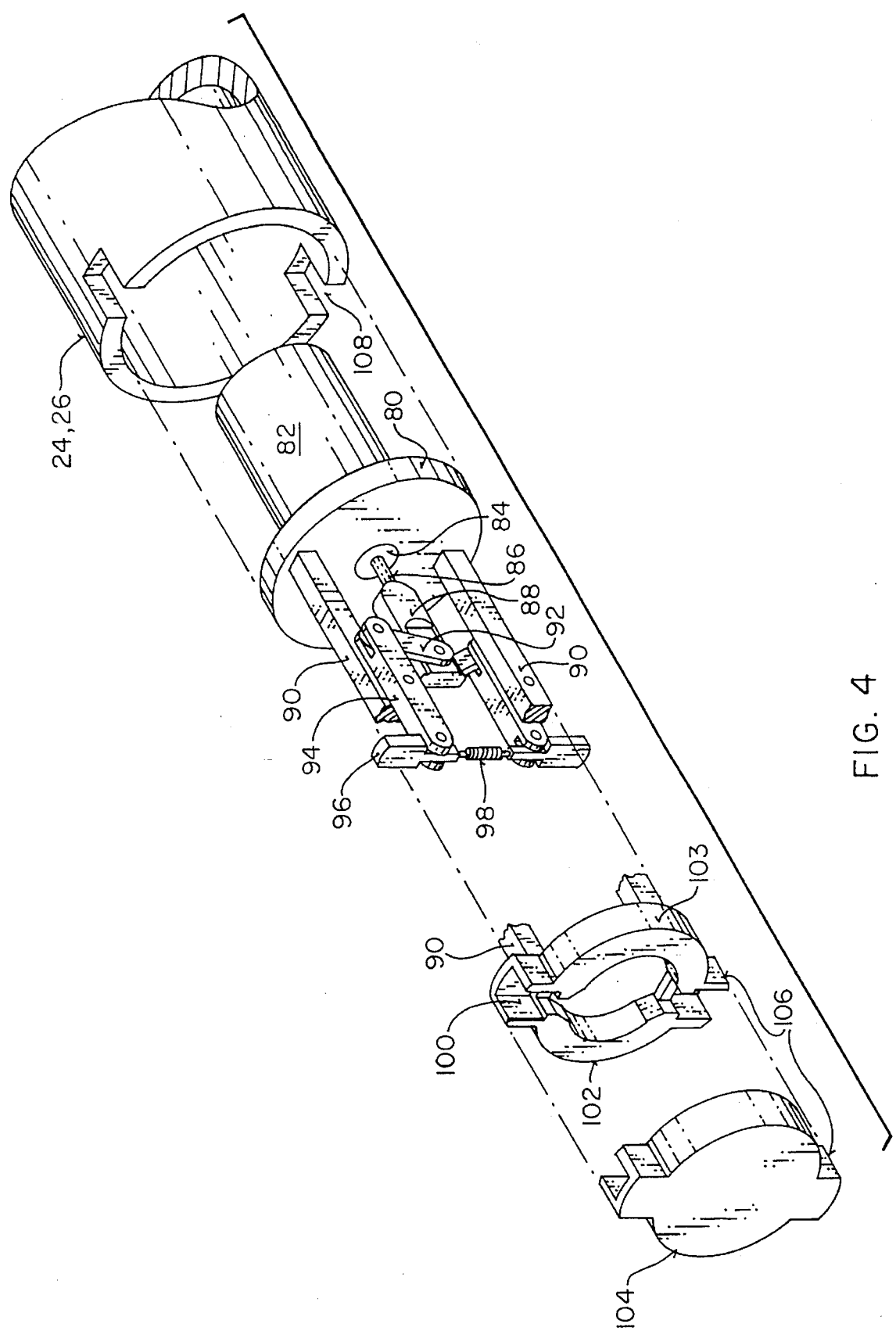
FIG. 4 is an exploded detailed view of the locking mechanism of the telescoping segments of the horizontal arm.

Referring now to FIG. 4, the structure of horizontal arm locking mechanisms 58, 60 will be more fully described. Locking means 58, 60 include a mounting frame 102 comprising a solenoid mounting plate 80, support bars 90 and backplate 103. Solenoid 82 threadably engages hole 84 in solenoid mounting plate 80. Piston 86 of solenoid 82 is coupled to linkage mount 88. Links 92 extend between linkage mount 88 and links 94, links 94 being pivotally pinned to support bars 90. At the distal ends of links 94, shoes 96 are pinned. Spring 98 applies a tensile force between opposing shoes 96. Shoes 96 are disposed within aperture 100 of backplate 103. Faceplate 104, of a configuration matching that of backplate 103, is affixed to the distal surface of backplate 103. Locking means 58, 60 are disposed within the proximal ends of segments 24, 26 with the flanges 106 on faceplate 104 and backplate 102 seating within aperture 108 in the ends of segments 24, 26.

Locking means 58, 60 are configured so as to be in the "locked" position when no power is applied to the solenoid 82. Thus, in the absence of electrical power to solenoid 82, spring 98 forces shoes 96 radially through apertures 100 in backplate 103 and faceplate 104 and through apertures 108 in segments 24, 26, the shoes 96 fictionally engaging the interior surface of segments 22, 24 respectively. When power is supplied to solenoid 82, piston 86 retracts, pulling on links 92 thereby causing shoes 96 to be retracted away from the interior surfaces of segments 22, 24.

Alternatively, the means for releasably locking comprises friction-inducing means within segments 22, 24, 26 which lock the segments in a radial position when the distal end of the arm is loaded. Usually, such loading is induced simply by coupling end-of-arm tooling mounted on end segment 28 to a part of a patient's body, and raising the lifting means. This imparts a downward force to the distal end of the horizontal arm, which is translated into frictional forces between the exterior surfaces of segments 24, 26 and the interior surfaces of segments 22, 24, respectively. The frictional forces are sufficient to resist radial movement of the segments, thereby locking the arm in a radial position.

FIGS. 5A–5C illustrate one embodiment of the end segment locking mechanism, which will now be more fully described. Outer frame 126 is coupled to the distal end of segment 26. In various exemplary embodiments, outer frame 126 can be rigidly fixed, rotationally coupled for either one- or two-axis rotation, or mounted using a ball-and-socket joint to the end of segment 26. End portion 134 is affixed to inner frame 136, inner frame 136 being rotatably mounted within outer frame 126 by axle bearings 128. The locking mechanism includes solenoid 112 mounted to plate 114. Links 116, 118 are coupled to linkage mount 115 which is attached to piston 113 of solenoid 112. Lateral links 120 extend from links 118 to shoes 122. Spring 130 applies a compressive force against opposing links 120, pushing shoes 122 into aperture 124 and against the inner surface of inner frame 136. The frictional force between shoes 122 and frame 136 provides positional locking of the end segment.

In a preferred embodiment, the end segment includes actuator switches 40, 42 controlling motor 62 in vertical post 12 to provide the raising or lowering of the horizontal arm 14. Locking actuator switch 44 is disposed on the side surface of distal portion 134 of end segment 28 to provide actuation of the locking mechanisms. Mounting means 46, 47 are provided at the distal end of end segment 28. Mounting means 46, 47 include a tapered dovetail aperture 132 into which end of arm tooling or surgical instruments with a corresponding mounting configuration can be inserted.

Figure 5D:
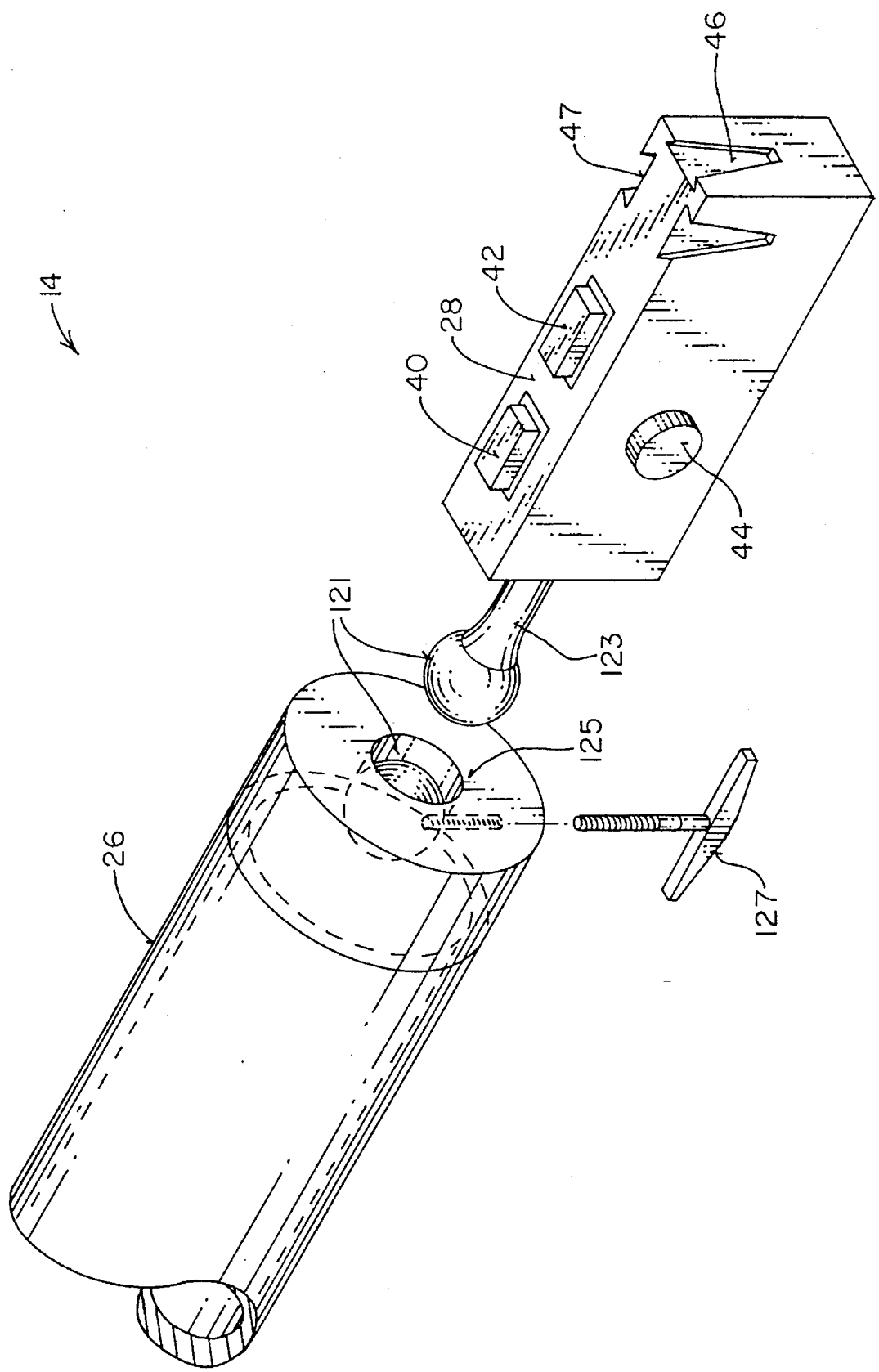
FIG. 5D is a perspective assembly view of an end segment of the positionable support structure of FIG. 1.

FIG. 5D illustrates another embodiment of end segment 28. In this embodiment, end segment 28 is coupled to segment 26 of the arm by a ball and socket joint 121, with end segment 28 fixed to ball 123, and socket 125 mounted at the distal end of segment 26. A clamp 127 is provided for locking the end segment in position, which may comprise a set screw as illustrated, a pneumatic clamping device disposed in segment 26, or other known clamping means.

Figure 6:
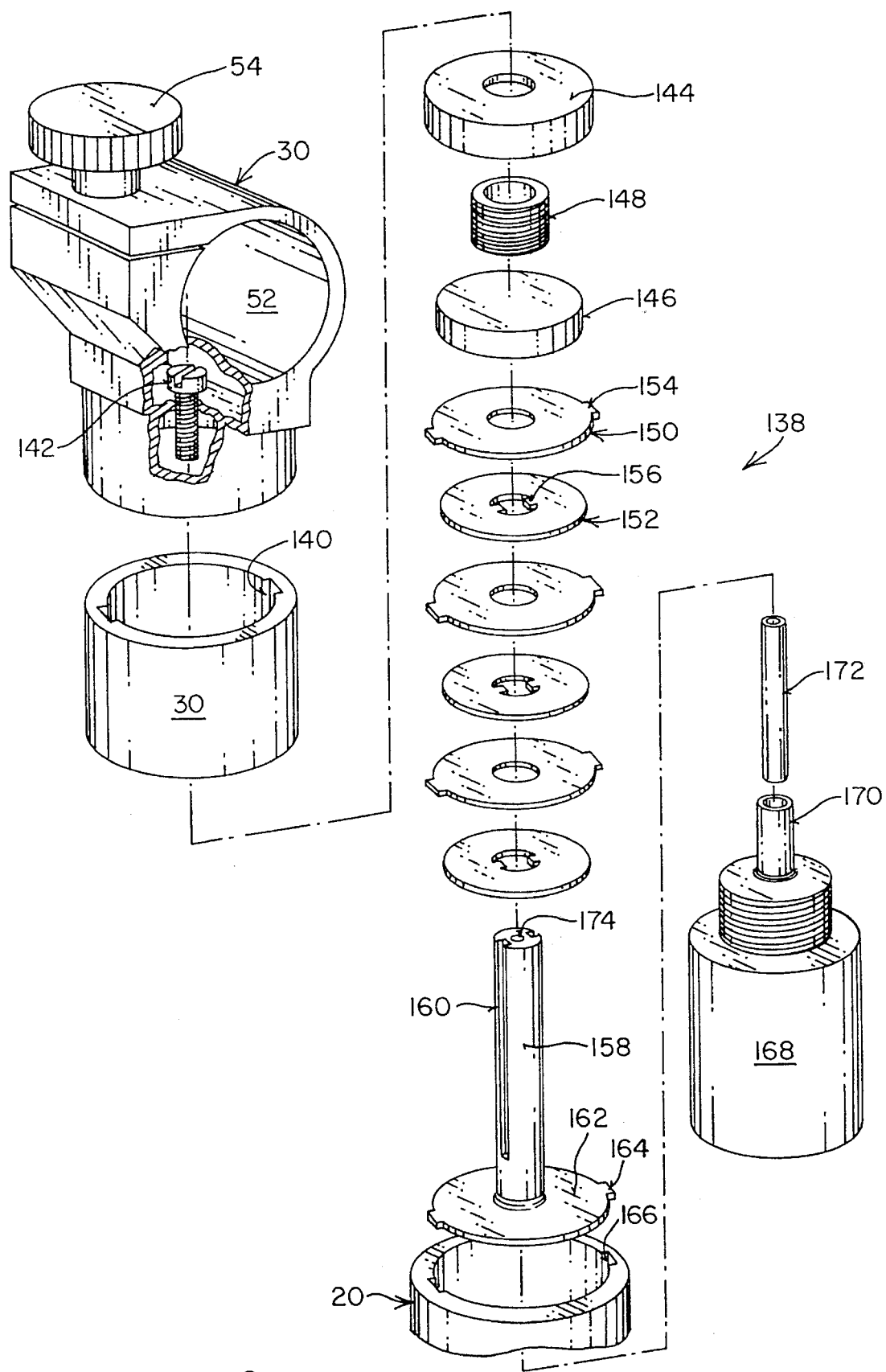
FIG. 6 is an exploded detailed view of the rotational locking means in the vertical post.
Figure 7:
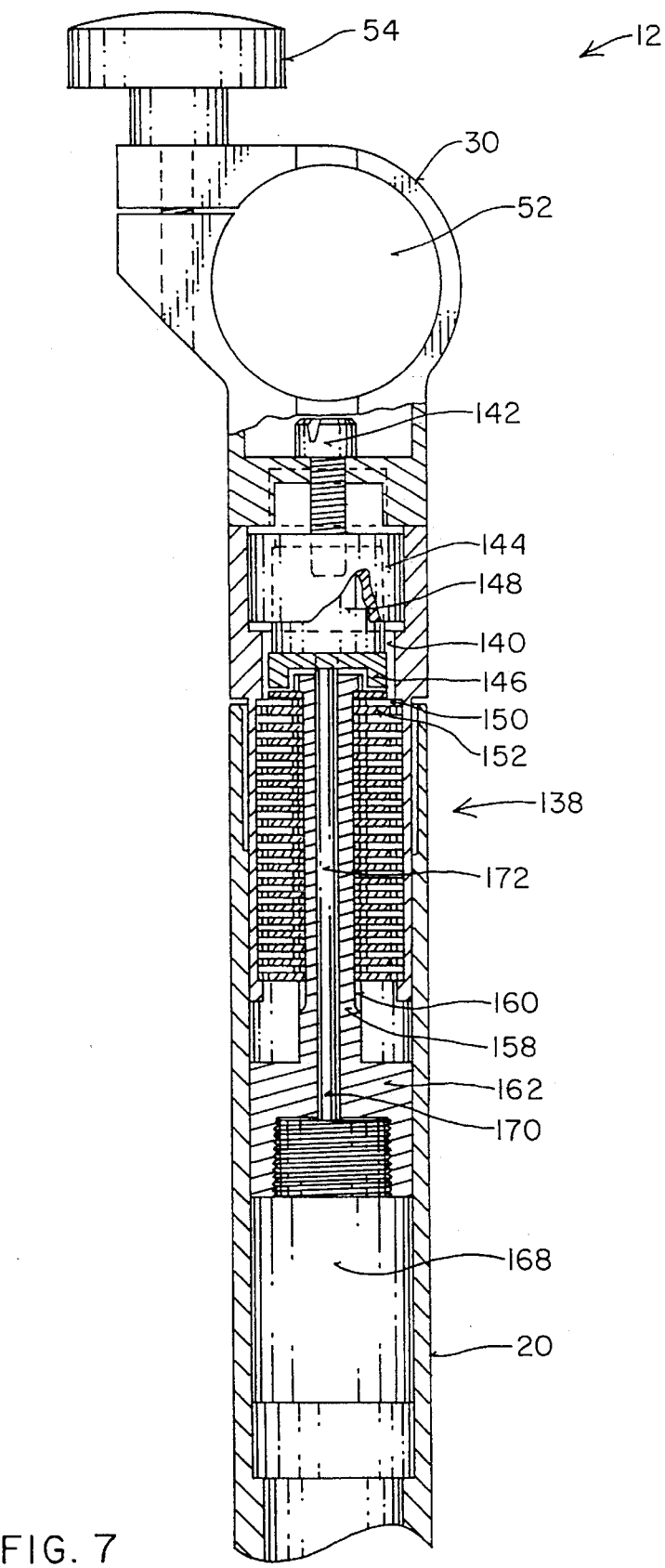
FIG. 7 is a side cross-sectional view of the top portion of the vertical post showing the rotational locking means.

Referring now to FIG. 6, the rotational locking mechanism for the horizontal arm will be more fully described. The rotational locking mechanism 138 includes a pedestal 162 with opposing lateral flanges 164 engaging with channels 166 in segment 20. Spindle 158 extends upwardly from pedestal 162, having opposing channels 160 extending longitudinally from the upper end of spindle 158 along a portion of its length. Friction disks 154, 156 are stacked over spindle 158, such that inward extending flanges 156 engage in channels 160. Outward extending flanges 154 in disks 150 engage in channels 140 of frame 30. Disk retainer 146 engages the uppermost disk on its lower surface. A spring 148 held in place by spring retainer 144 applies compressive force against disk retainer 146 and disks 150, 152 stacked below it on spindle 158. Adjustment screw 142 through frame 30 provides for adjustment of the compressive force of spring 148 on disks 150, 152. Solenoid 168 is threadably attached to the lower surface of pedestal 162 with piston 170 and rod 172 extending through hole 174 in spindle 158. The upper end of rod 172 contacts the lower surface of disk retainer 146. Preferably, when no power is applied to the solenoid, it is in a retracted position, allowing spring 148 to compress disks 150, 152, thereby locking the rotational position of the horizontal arm. When power is applied to solenoid 168, retainer 146 is pushed upward by piston 170 and rod 172, relieving the friction force from disks 150, 152, allowing horizontal arm 14 to be rotated relative to vertical post 12.

Figure 8:
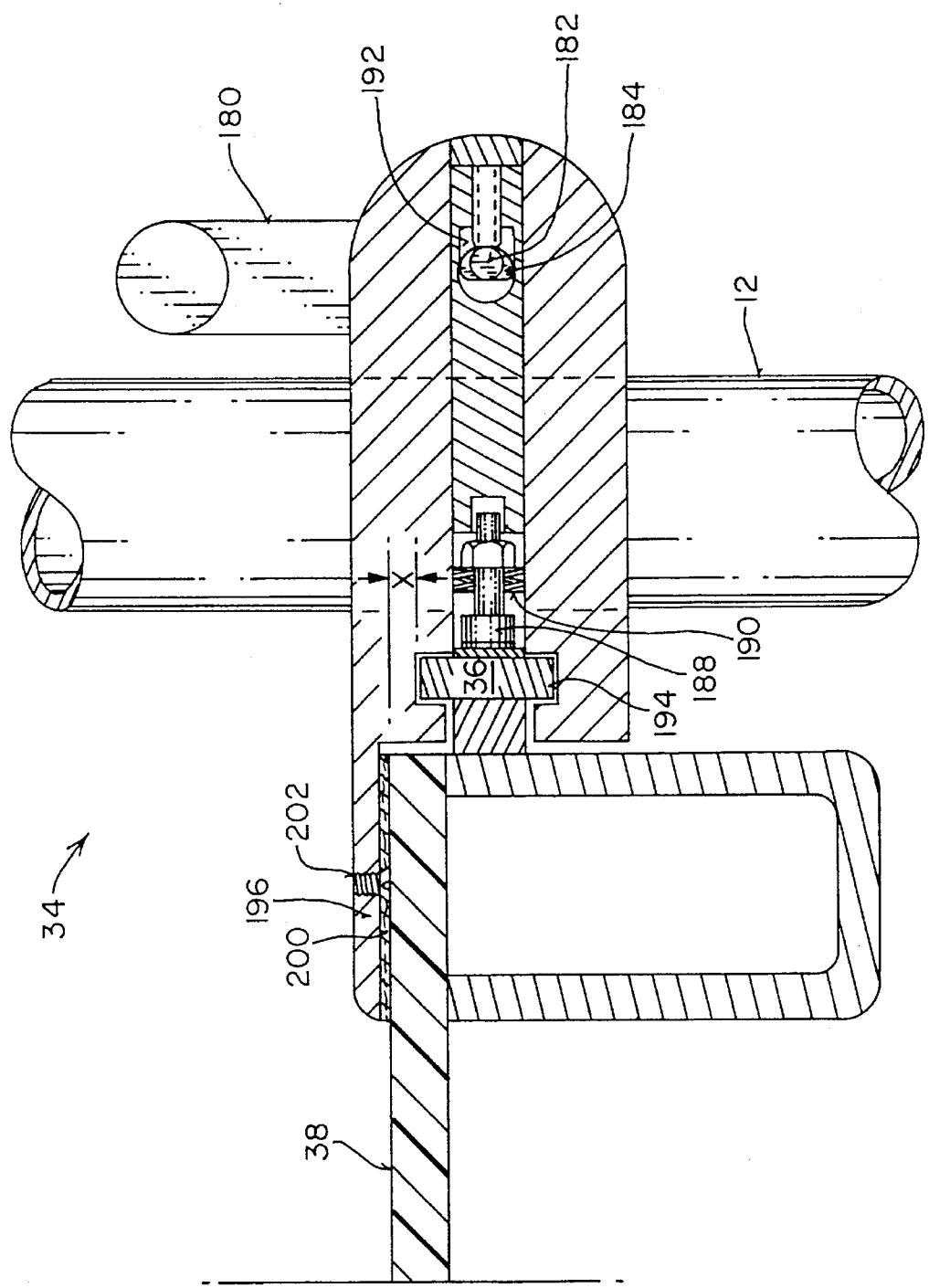
FIG. 8 is a side elevational view of the means for clamping the support structure of FIG. 1 to a surgical table.
Figure 9:
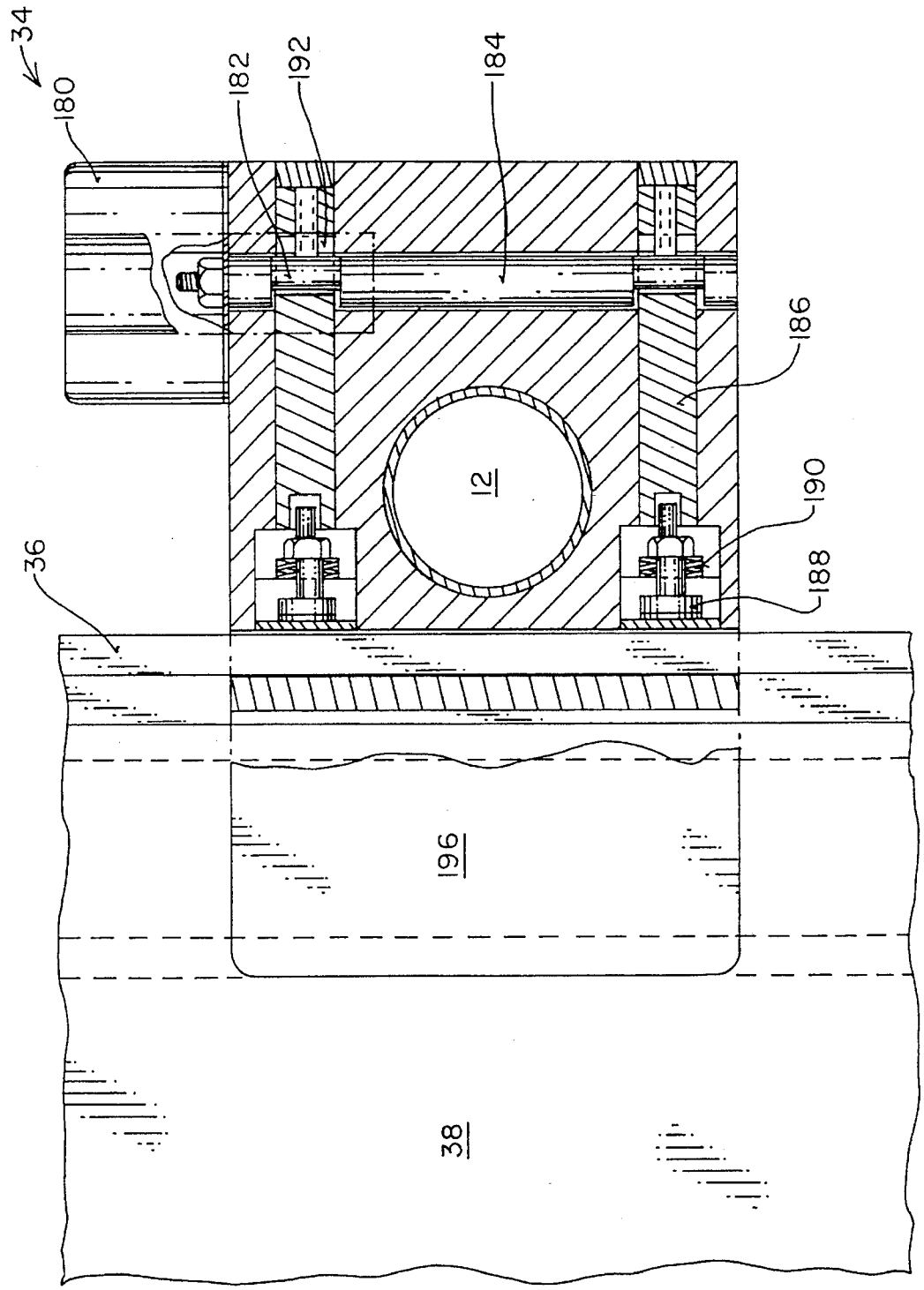
FIG. 9 is a top view of the means for clamping the support structure of FIG. 1 to a surgical table.

Referring to FIGS. 8 and 9, the structure of the table clamping mechanism 34 will be more fully described. Channel 194 engages rail 36 of surgical table 38, allowing clamping means 34 to be located at a desired point along the rail 36. Stabilizing plate 196 provides horizontal stability for the positionable support structure. Because there may be some variation in the distance "X" between the top of rail 36 and the surface of table 38, shims 200 are provided which lie between plate 196 and the top surface of table 38. Shims 200 are fastened to plate 196 by screws 202, and may be provided in various thicknesses, allowing the shims to be interchanged according to the distance "X" of various tables.

Handle 180 is coupled to shaft 184 extending through the rearward portion of clamp means 34 parallel to rail 36. The shaft 184 includes a pair of separated cams 182 engaging rods 186. Shoes 188 are attached to the ends of rods 186 with compression springs 190 providing compressive flexibility. When handle 180 is rotated 180°, cams 182 change orientation so as to push rods 186 against shoes 188, which engage rail 36.

Figure 10:
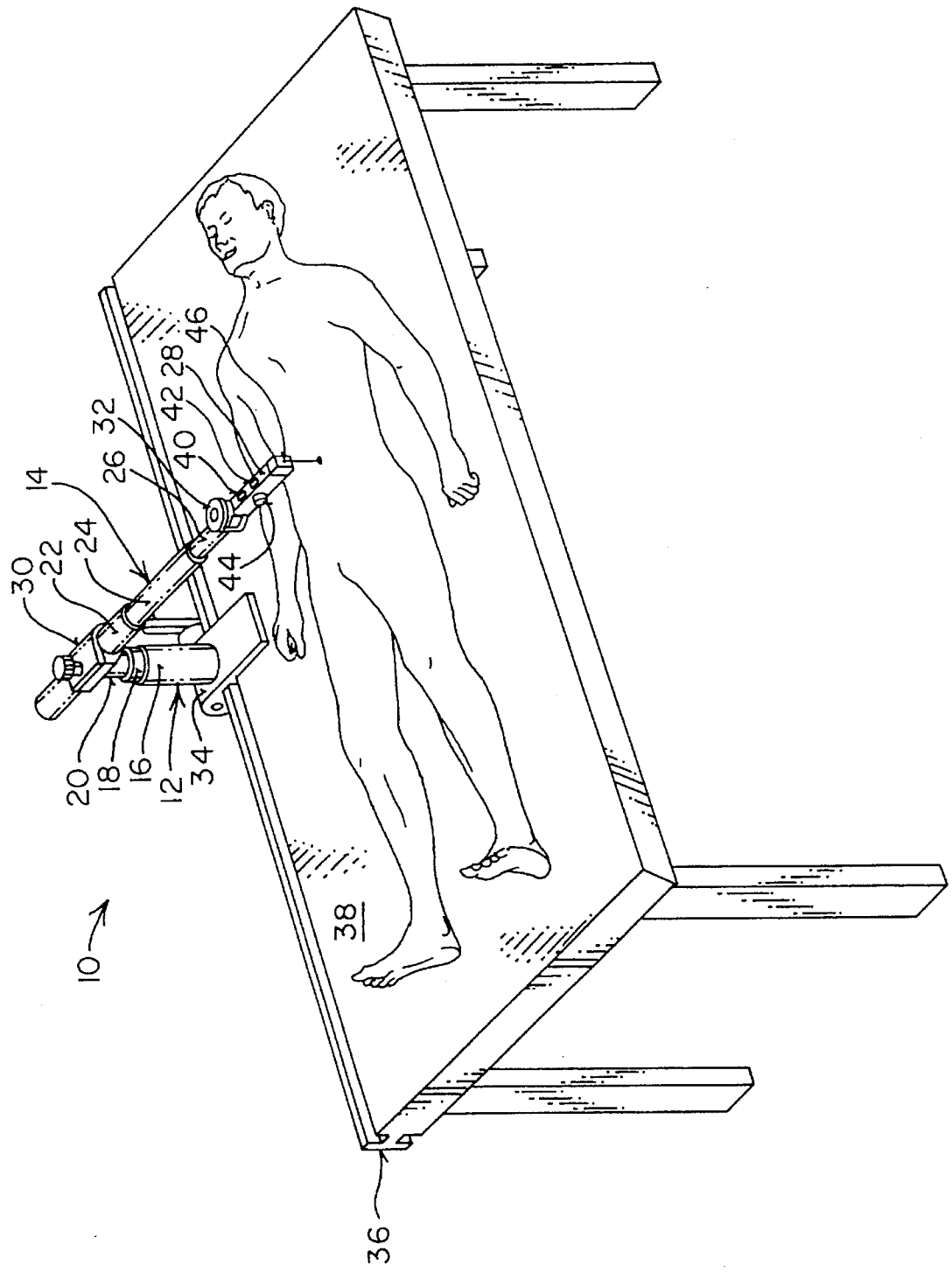
FIG. 10 is a perspective view illustrating the method of the present invention for peritoneal distension, wherein the positionable support structure is in a horizontally aligned but vertically lowered position.
Figure 11:
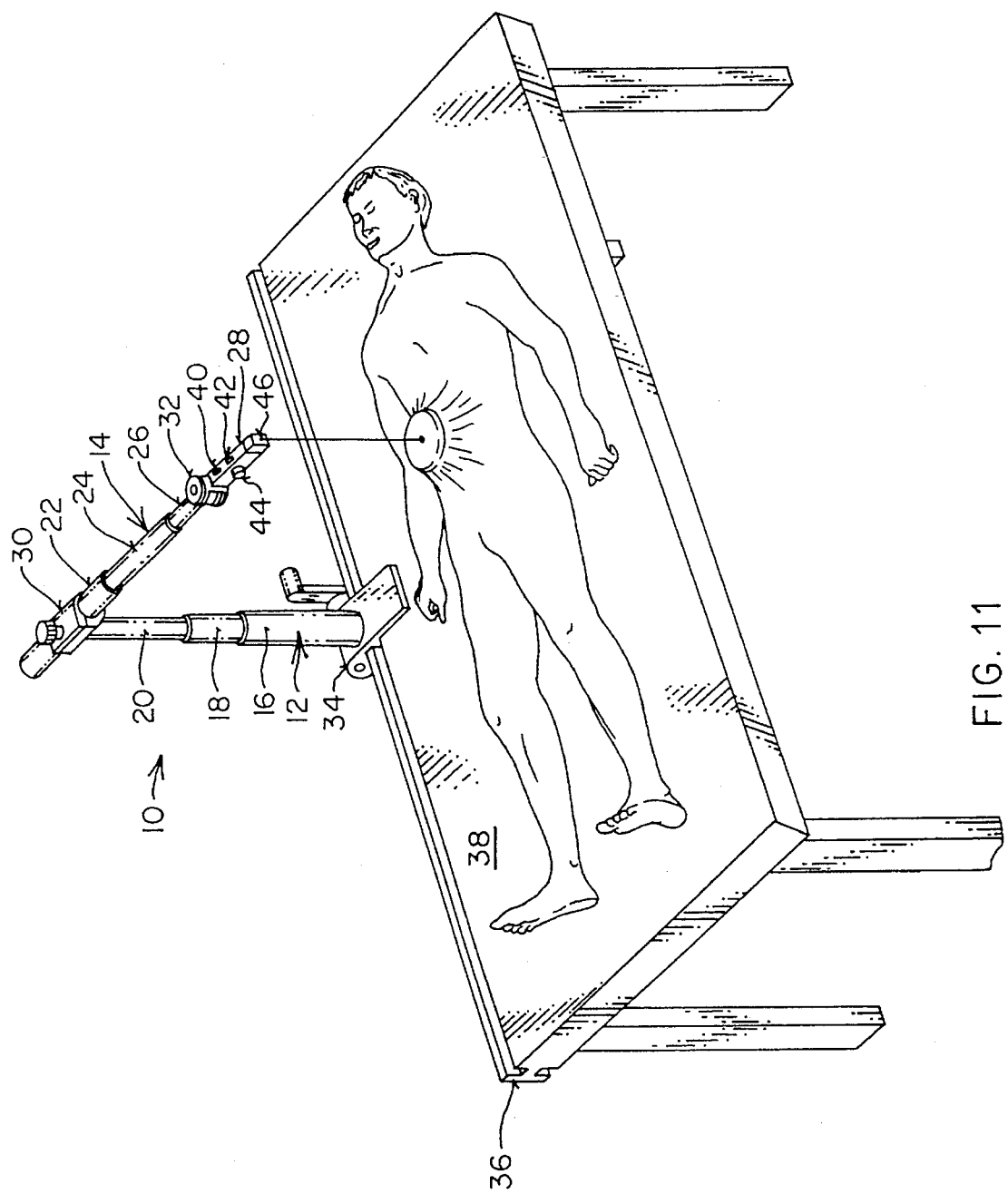
FIG. 11 is an illustration of the method of the present invention, wherein the positionable support structure is in a vertically raised position with the peritoneum of the patient distended.
Figure 12:
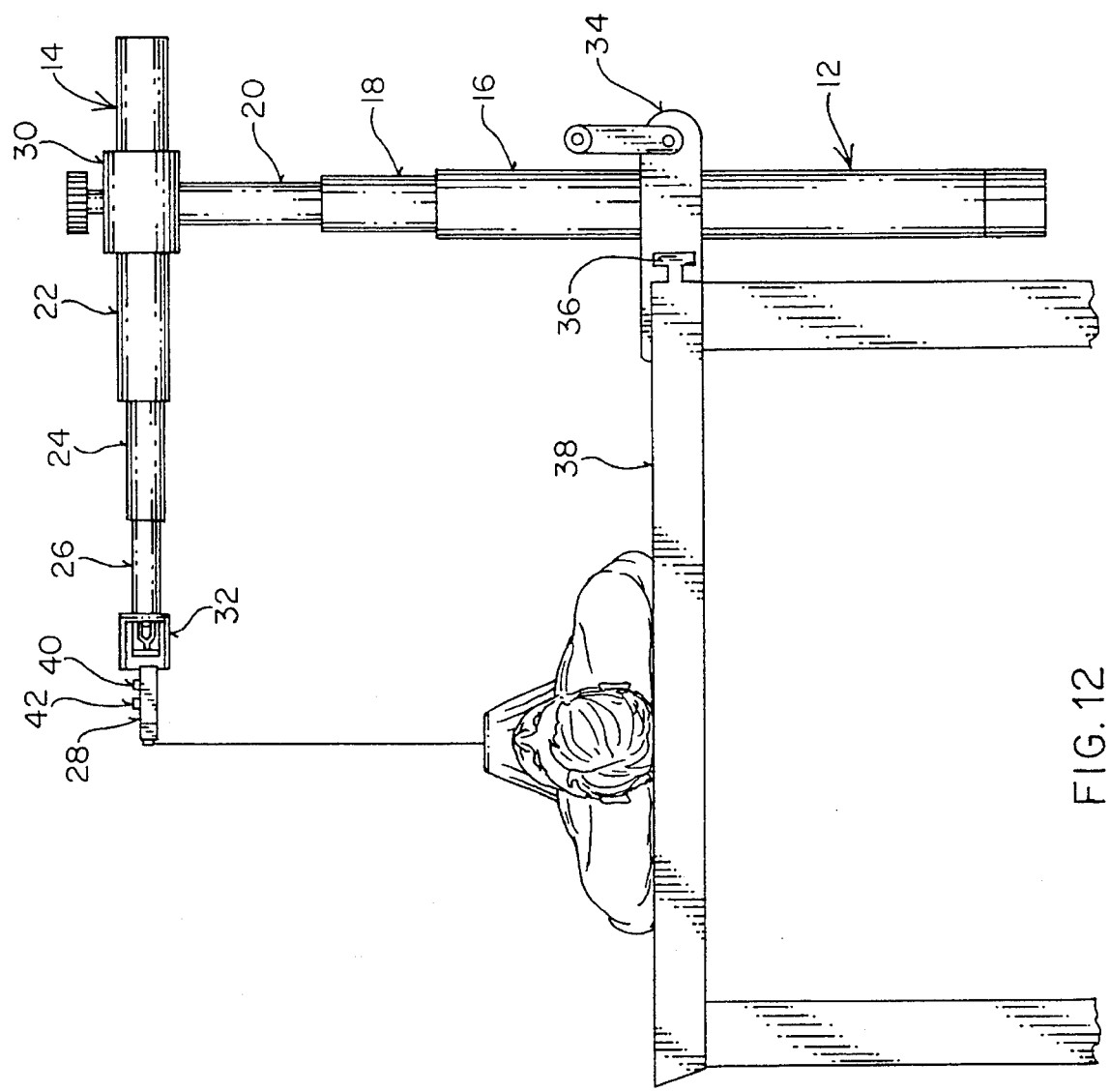
FIG. 12 is a side elevational view of the positionable support structure mounted to a surgical table showing the positionable support structure in a vertically raised extended position distending the peritoneum of the patient.

Referring now to FIGS. 10–12, use of the positionable support structure 10 for performing peritoneal distention will be described. The horizontal arm of the support structure is positioned over a desired point on the patient's body, usually over the lower abdomen. This may be performed by grasping the horizontal arm and depressing switch 44 to release the locking mechanisms, then rotating or extending the arm to the desired location. Once the arm is in position, locking actuator switch 44 is released so as to re-lock the arm in position. Peritoneal distension instruments, which usually will extend through an incision in the abdomen of the patient, are attached to the mounting means 46 on end segment 28, by sliding the dovetail mount on such instruments into aperture 132 at the distal end of end segments 28. To distend the peritoneum of the patient, the user presses actuator switch 40 on end segment 28 which activates motor 62, extending vertical post 12 and raising horizontal arm 14. The resulting configuration is shown in FIGS. 11 and 12.

In a preferred embodiment, the positionable support structure includes a load limiting means, wherein if a selected load limit is exceeded, the electric motor will not operate to extend the post. This provides the safety feature of preventing extension of the vertical post beyond that necessary to obtain the desired peritoneal distension. Preferably, the load limiting means comprises either a force sensor and a cut-off switch, or a motor load sensor. In still another embodiment, the load on the arm is communicated to the user by an indicator, for example, a display or meter. In other embodiments, the load limiting means is adjustable to various load limits, or may be defeated by the user.

In a further preferred embodiment, the locking mechanisms have a force limit which, when exceeded, will release the locking mechanisms allowing the arm to move. This allows the operator to forcibly move the support structure from a loaded position in the event of a power failure or emergency. In a preferred embodiment, the force limit will be provided by the locking force limitations of the solenoids and friction force limitations of the shoes of the locking mechanisms.

While the invention has been described with reference to a specific embodiment, the description is illustrative of the invention and is not to be construed as limiting the invention. Various modifications and applications may occur to those skilled in the art without departing from the true spirit and scope of the invention as defined by the appended claims.

What is claimed is:

1. A positionable support structure adapted to be mounted on a table, said support structure comprising:

an extendible vertical post having a lower end and an upper end and comprising plurality of telescoping vertical segments;

means for removably securing the lower end of the vertical post to the table;

an extendible arm extending generally horizontally from the vertical post and having a proximal end and a distal end, said proximal end being pivotally secured to the a distal end, said proximal end being pivotally secured to the upper end of the vertical post, whereby the horizontal arm can be rotated about an axis defined by the vertical post;

means for releasably locking the position of the horizontal arm relative to the vertical post; and means for vertical extension and retraction of the vertical post while the horizontal arm remains locked relative to the vertical post.

2. A positionable support structure as in claim 1, wherein said means for releasably locking includes an actuation switch disposed on the distal end of the horizontal arm.

3. A positionable support structure as in claim 1, wherein said means for power-assisted vertical extension and retraction includes an actuation switch disposed on the distal end of the horizontal arm.

4. A positionable support structure as in claim 1 further comprising an end segment pivotally attached to the distal end of the horizontal arm.

5. A positionable support structure as in claim 1 wherein the extendible horizontal arm comprises a plurality of telescoping horizontal segments.

6. A positionable support structure as in claim 5 wherein the means for releasably locking comprises friction-inducing means in said telescoping horizontal segments for locking said arm in a radial position, said friction-inducing means responsive to loading at the distal end of the horizontal arm.

7. A positionable support structure as in claim 5 wherein said means for releasably locking includes means for rotationally locking said horizontal arm in position relative to said vertical post.

8. A positionable support structure adapted to be mounted on a table, said support structure comprising:

an extendible vertical post having a lower end and an upper end, said extendible vertical post comprising a plurality of telescoping vertical segments;

means for removably securing the lower end of the post to the table;

an extendible horizontal arm having a proximal end and a distal end, said extendible horizontal arm comprising a plurality of telescoping horizontal segments, wherein said proximal end is pivotally secured to the upper end of the extendible vertical post such that the extendible horizontal arm can be rotated about an axis defined by the post;

an end segment pivotally attached to the distal end of the horizontal arm;

means for releasably locking the relative positions of the vertical post, horizontal arm, and end segment; and means for power-assisted extension of the vertical post, said means including an actuator switch mounted on the end segment.

9. A positionable support structure as in claim 8 wherein the means for releasably locking comprises locking mechanisms mounted interior to said horizontal segments for locking said arm in a radial position.

10. A positionable support structure as in claim 9 wherein said means for releasably locking includes means for rotationally locking said horizontal arm in position relative to said vertical post.

11. A positionable support structure as in claim 10 wherein said means for rotationally locking comprises a plurality of discs in a stacked relationship, a first selected number of said discs being fixed to said horizontal arm and a second selected number of said discs being fixed to said vertical post, and means for fictionally engaging said first selected number with said second selected number.

12. A positionable support structure as in claim 10, further comprising means for releasably locking said end segment in position relative to the horizontal arm.

13. A positionable support structure as in claim 9 wherein said means for releasably locking include an electric solenoid configured so that the horizontal arm is locked in position when no current is applied to said solenoid and the horizontal arm is movable when current is applied to the solenoids.

14. A positionable support structure as in claim 12 wherein said means for releasably locking includes an electric solenoid configured so that the end segment is locked in position when no current is applied to said solenoid and the end segment movable when current is applied to the solenoids.

15. A positionable support structure as in claim 9 further comprising a switch on the end segment for actuating the locking mechanisms.

16. A positionable support structure as in claim 8 wherein the means for releasably locking comprises friction-inducing means in said telescoping horizontal segments, said friction-inducing means responsive to loading at the distal end of the horizontal arm.

17. A positionable support structure as in claim 8 wherein the means for power-assisted extension and retraction includes an electric motor.

18. A positionable support structure as in claim 8 wherein the end segment includes means for mounting tooling thereon.

19. A positionable support structure as in claim 18 wherein the means for mounting allows the tooling mounted thereon to move upward in response to an upward force applied against it.

20. A positionable support structure as in claim 18 further comprising draping means removably covering said vertical post and horizontal arm for isolating the support structure from the surrounding atmosphere, said draping means coupling to said means for mounting.

21. A positionable support structure as in claim 8 wherein the means for releasably locking has a force limit allowing the horizontal arm and end segment to be moved when a force greater than the force limit is applied.

22. A positionable support structure as in claim 8 wherein said means for power-assisted extension and retraction has a selectable load limit preventing said vertical post from further extension when said load limit is exceeded.

23. A positionable support structure as in claim 8 wherein the end segment is attached to the horizontal arm by a rotary joint, said rotary joint comprising:

a hub fixed to the horizontal arm; and an axle held by the hub, the end segment being fixed to the axle.

24. A positionable support structure as in claim 8 wherein the end segment is attached to the horizontal arm by a ball-and-socket joint.

25. A positionable support structure as in claim 8 wherein said horizontal segments include means for preventing rotation of said segments relative to each other.

26. A positionable support structure adapted to be mounted on a table, said support structure comprising:

an extendible vertical post having a lower end and an upper end;

means for removably securing the lower end of the vertical post to a table;

an extendible arm extending generally horizontally from the vertical post and having a proximal end and a distal end, said proximal end being pivotally secured to the upper end of the vertical post and comprising a plurality of telescoping horizontal segments, whereby the horizontal arm can be rotated about an axis defined by the vertical post;

means for releasably locking the position of the horizontal arm relative to the vertical post; and means for vertical extension and retraction of the vertical post while the horizontal arm remains locked relative to the vertical post.

27. A positionable support structure as in claim 26, wherein said means for releasably locking includes an actuation switch disposed on the distal end of the horizontal arm.

28. A positionable support structure as in claim 26, wherein said means for power-assisted vertical extension and retraction includes an actuation switch disposed on the distal end of the horizontal arm.

29. A positionable support structure as in claim 26 further comprising an end segment pivotally attached to the distal end of the horizontal arm.

30. A positionable support structure as in claim 26 wherein the extendible vertical post comprises a plurality of telescoping vertical segments.

31. A positionable support structure as in claim 26 wherein the means for releasably locking comprises friction-inducing means in said telescoping horizontal segments for locking said arm in a radial position, said friction-inducing means responsive to loading at the distal end of the horizontal arm.

32. A positionable support structure as in claim 26 wherein said means for releasably locking includes means for rotationally locking said horizontal arm in position relative to said vertical post.

* * * * *